(12) United States Patent
Steinberg (10) Patent No.: US 7,054,413 B2
(45) Date of Patent: May 30, 2006

(54) ROTATABLE MULTI-ELEMENT BEAM SHAPING DEVICE

(75) Inventor: Todd Howard Steinberg, Martinez, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 579 days.

(21) Appl. No.: 09/809,926

(22) Filed: Mar. 15, 2001

(65) Prior Publication Data

US 2002/0131556 A1    Sep. 19, 2002

(51) Int. Cl.
*G21K 1/04* (2006.01)
(52) U.S. Cl. .................. 378/152; 378/153; 378/147; 378/150
(58) Field of Classification Search ........ 378/152–153, 378/147, 204, 150, 65, 148

See application file for complete search history.

(56) References Cited

U.S. PATENT DOCUMENTS

| | | | |
|---|---|---|---|
| 4,868,844 A * | 9/1989 | Nunan | 378/147 |
| 5,165,106 A | 11/1992 | Barthelmes et al. | 250/505.1 |
| 5,442,675 A * | 8/1995 | Swerdloff et al. | 378/150 |
| 5,591,983 A | 1/1997 | Yao | 250/505.1 |
| 5,684,854 A * | 11/1997 | Hughes | 378/151 |
| 5,748,703 A * | 5/1998 | Cosman | 378/147 |
| 6,041,101 A * | 3/2000 | Kooy et al. | 378/147 |

* cited by examiner

*Primary Examiner*—Andrew Schechter
*Assistant Examiner*—George Y. Wang (57) ABSTRACT

A rotatable multi-element beam shaping device according to embodiments of the invention includes a first assembly, rotatable about a central axis through which a beam passes. The first assembly has a first and a second jaw adapted to move across the central axis to shape the beam. A second assembly, positioned below the first assembly, is also rotatable about the central axis, and has a third and a fourth jaw adapted to move across the central axis to further shape the beam. The first and the second assemblies, according to the invention, are separately controllable.

25 Claims, 5 Drawing Sheets

ROTATABLE MULTI-ELEMENT BEAM SHAPING DEVICE

BACKGROUND OF THE INVENTION

1. Field of the Invention

The present invention relates generally to radiation therapy devices, and more particularly, to a rotatable multi-element beam shaping device for use in a radiation therapy device.

2. Description of the Related Art

Conventional radiation therapy typically involves directing a radiation beam at a tumor in a patient according to deliver a predetermined dose of therapeutic radiation to the tumor according to an established treatment plan. This is typically accomplished using a radiation therapy device such as the device described in U.S. Pat. No. 5,668,847 issued Sep. 16, 1997 to Hernandez, the contents of which are incorporated herein for all purposes.

Tumors have three-dimensional treatment volumes which typically include segments of normal, healthy tissue and organs. Healthy tissue and organs are often in the treatment path of the radiation beam. This complicates treatment, because the healthy tissue and organs must be taken into account when delivering a dose of radiation to the tumor. While there is a need to minimize damage to healthy tissue and organs, there is an equally important need to ensure that the tumor receives an adequately high dose of radiation. Cure rates for many tumors are a sensitive function of the dose they receive. Therefore, it is important to closely match the radiation beam's shape and effects with the shape and volume of the tumor being treated.

In many radiation therapy devices, the treatment beam is projected through a pre-patient collimating device (a "collimator"), that defines the treatment beam profile or the treatment volume at the treatment zone. A number of different collimator techniques have been developed to attempt to conform the dose rate and the treatment volume to the shape of the tumor while taking nearby healthy tissue and organs into account. A first technique is to use a collimator with solid jaw blocks positioned along a path of the treatment beam to create a field shape based on the shape of the tumor to be treated. Typically, two sets of blocks are provided, including two blocks making up a Y-jaw generally disposed parallel to a Y-axis (with the Z-axis being parallel to the beam path), and two blocks making up an X-jaw generally disposed parallel to an X-axis. The X-jaw is conventionally placed between the Y-jaws and the patient.

These solid jaw blocks, however, do not provide sufficient variability in the field shape. In particular, where the tumor has a shape which requires a field edge relatively parallel to the edge of the jaw blocks, the edge of the jaw block becomes more predominant in forming the field edge. As a result, undulation of the field increases as well as the effective penumbra. This can be particularly difficult where the treatment beam is an X-ray beam. It is also difficult to adjust the field shape where the treatment beam is an electron beam due to electron attenuation and scattering.

Multileaf, or "multielement" block collimators were developed to provide more variation and control over the shape of the field at the treatment zone. An example multielement collimator is described in U.S. Pat. No. 5,591,983 issued to Hughes on Jan. 7, 1997. The Hughes collimator uses an X-jaw which has two blocks each made up of a number of individual elements. Each of the elements of the X-jaw can be moved longitudinally across the path of the radiation beam to create a desired beam shape at the point of treatment.

Further control over the shape of the beam is desirable. Existing block collimators fix the position of the Y-jaw with respect to the X-jaw, that is, the Y-jaw blocks do not move independently of the X-jaw blocks. As a result, many treatments involve tumors having a shape relatively parallel to one or more edges of either the X- or Y-jaws. Delivery of an appropriate therapeutic dose of radiation to these tumors can be difficult due to radiation scattering, undulation, and penumbra effects.

Therefore, it would be desirable to provide a system and method which allows further control of each of the blocks, each of the jaws, and each of the elements in a multielement collimator to increase control over the beam shape, including control over the penumbra and undulation effects which can arise when the treatment field edge becomes relatively parallel to edges of the blocks, jaws, and/or elements of the collimator. It would also be desirable to provide control over the beam shape to provide more accurate control during treatment to accommodate beam attenuation and scattering.

SUMMARY OF THE INVENTION

A rotatable multi-element beam shaping device according to embodiments of the invention includes a first assembly, rotatable about a central axis through which a beam passes. The first assembly has a first and a second jaw adapted to move across the central axis to shape the beam. A second assembly, positioned below the first assembly, is also rotatable about the central axis, and has a third and a fourth jaw adapted to move across the central axis to further shape the beam. The first and the second assemblies, according to the invention, are separately controllable. For example, the upper assembly may be rotated about the axis independently of the rotation of the lower assembly about the axis. The result is a beam shaping device which permits the generation of a beam shape which conforms to the shape of a treatment zone on a patient, particularly with reduced penumbra and undulation values for the beam shape.

In one embodiment, beam shaping is further enhanced through the use of multiple, individually controlled elements in the second assembly. Each of the elements may be controlled to individually move across the central axis to shape the beam. In one embodiment, the elements are fitted together using tongue and grooves, and move using bearings located on alternating elements. In one embodiment, the elements are shaped to move in an arc across the axis, maintaining an element end distance from the beam source.

In one embodiment, the position of the first and second assemblies may be manipulated during a treatment to provide a dynamic approach to radiation therapy.

The present invention is not limited to the disclosed preferred embodiments, however, as those skilled in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts throughout the figures thereof, and wherein.

DETAILED DESCRIPTION

The following description is provided to enable any person skilled in the art to make and use the invention and sets forth the best modes contemplated by the inventor for carrying out the invention. Various modifications, however, will remain readily apparent to those skilled in the art.

Figure 1:
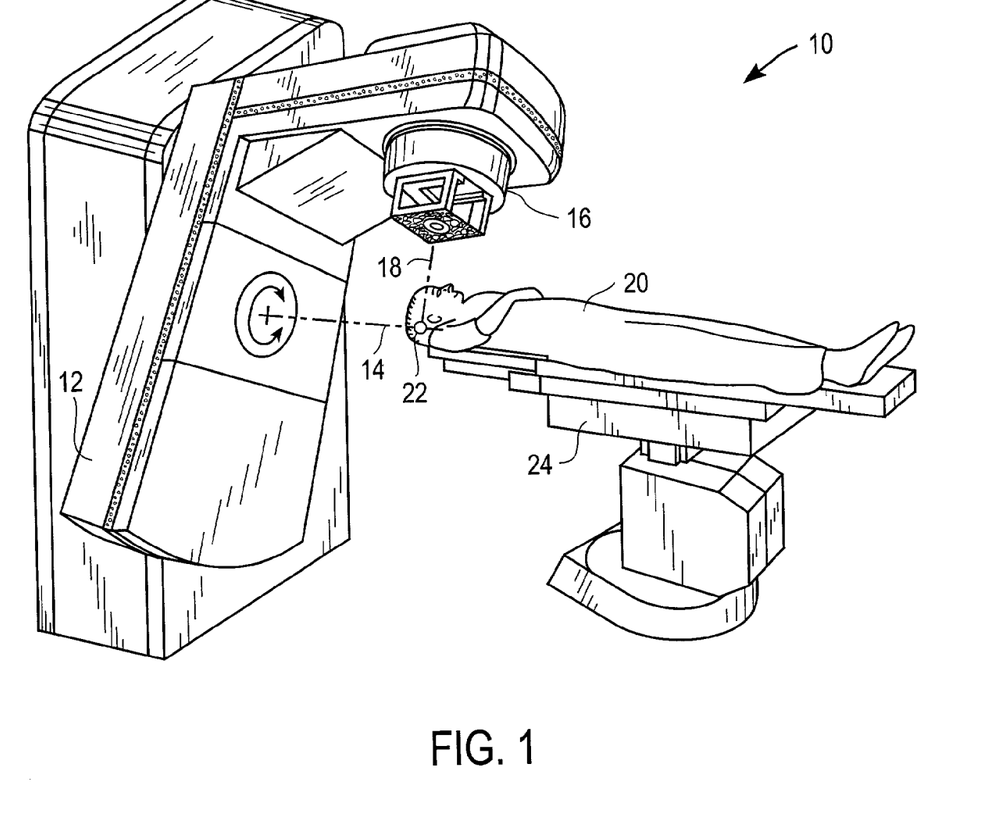
FIG. 1 is diagram illustrating a radiation therapy device.

Referring first to FIG. 1, a radiation therapy device 10 is shown in which embodiments of the present invention may be employed. Radiation therapy device 10 includes a gantry 12 which can be swiveled around a horizontal axis of rotation 14 in the course of a therapeutic treatment. A treatment head 16 of gantry 12 directs a radiation beam along axis 18 toward a patient 20. The radiation beam is typically generated by a linear accelerator positioned within gantry 12. The radiation beam may be electron or photon radiation. The radiation beam is trained on a treatment zone 22 of patient 20. Treatment zone 22 is an area which includes the tumor to be treated. Embodiments of the present invention permit the creation and control of the radiation beam to closely match the shape and size of the treatment zone 22.

Figure 2:
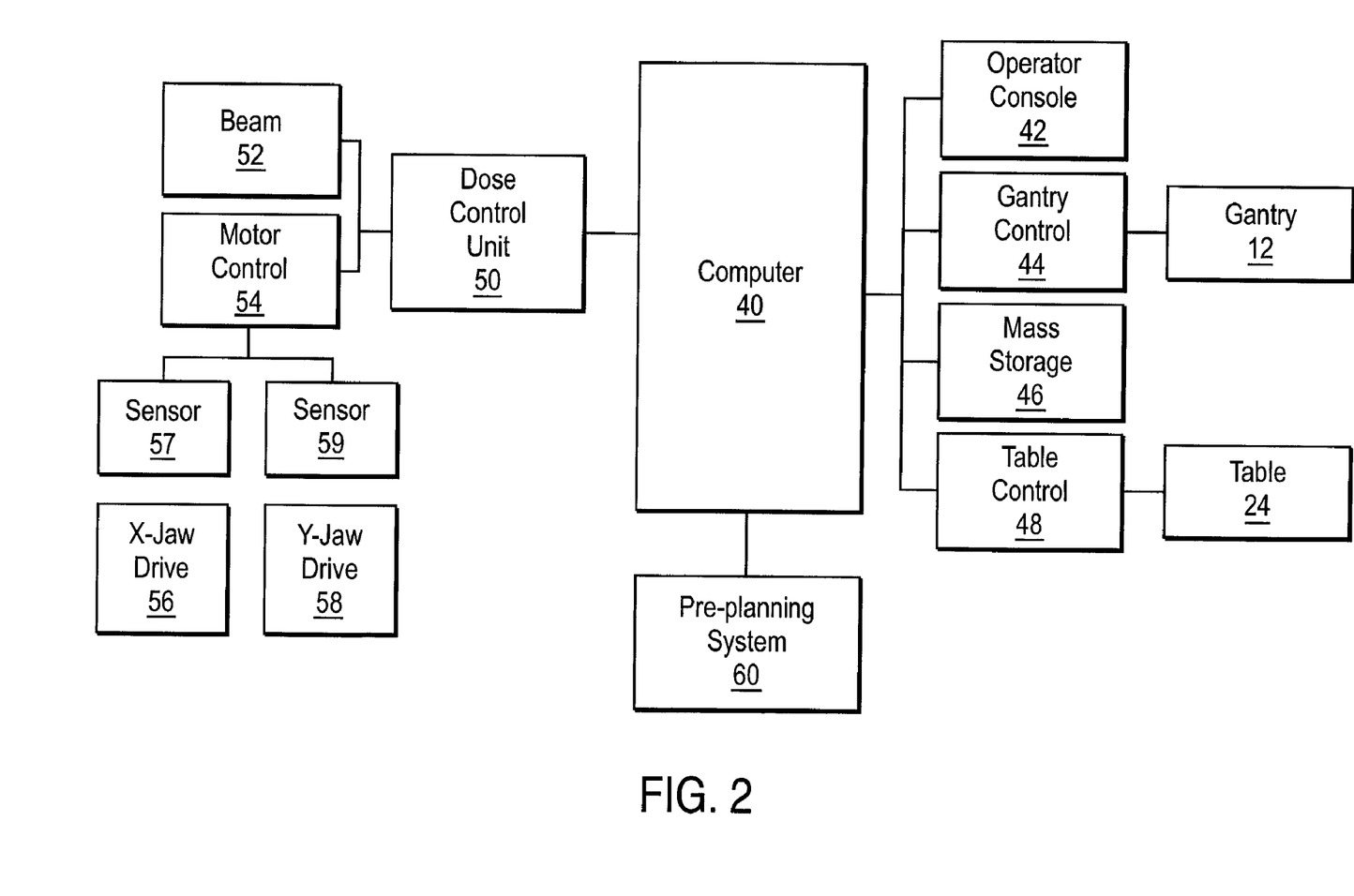
FIG. 2 is a block diagram illustrating portions of the radiation therapy device of FIG. 1 according to one embodiment of the present invention.

Referring now to FIG. 2, a block diagram is shown depicting a portion of a radiation therapy device 10 according to one embodiment of the present invention. In particular, treatment delivery elements of a radiation therapy device are shown, which may be configured in radiation therapy device 10 as depicted in FIG. 1. The treatment delivery elements include a computer 40, operatively coupled to an operator console 42 for receiving operator control inputs and for displaying treatment data to an operator. Operator console 42 is typically operated by a radiation therapist who administers the delivery of a radiation treatment as prescribed by an oncologist. Using operator console 42, the radiation therapist enters data that defines the radiation to be delivered to a patient.

Mass storage device 46 stores data used and generated during the operation of the radiation therapy device including, for example, treatment data as defined by an oncologist for a particular patient. This treatment data is generated, for example, using a pre-planning system 60 which may include manual and computerized inputs to determine a beam shape prior to treatment of a patient. Pre-planning system 60 is typically used to define and simulate a beam shape required to deliver an appropriate therapeutic dose of radiation to treatment zone 22. Data defining the beam shape and treatment are stored, e.g., in mass storage device 46 for use by computer 40 in delivering treatment.

Although a single computer 40 is depicted in FIG. 2, those skilled in the art will appreciate that the functions described herein may be accomplished using one or more computing devices operating together or independently. Those skilled in the art will also appreciate that any suitable general purpose or specially programmed computer may be used to achieve the functionality described herein.

Computer 40 is also operatively coupled to control units including a gantry control 44 and a table control 48. In operation, computer 40 directs the movement of gantry 12 via gantry control 44 and the movement of table 24 via table control 48. These devices are controlled by computer 40 to place a patient in a proper position to receive treatment from the radiation therapy device. In some embodiments, gantry 12 and/or table 24 may be repositioned during treatment to deliver a prescribed dose of radiation.

Computer 40 is also operatively coupled to a dose control unit 50 which includes a dosimetry controller and which is designed to control a beam 52 to achieve desired isodose curves. Beam 52 may be, for example, an X-ray beam or an electron beam. Beam 52 may be generated in any of a number of ways well-known to those skilled in the art. For example, dose control unit 50 may control a trigger system which generates injector trigger signals fed to an electron gun in a linear accelerator (not shown) which produces en electron beam 52 as output. Beam 52 is typically directed along an axis (as shown in FIG. 1 as item 18) toward treatment zone 22 on patient 20.

According to one embodiment of the invention, beam 52 is directed through a collimator assembly comprised of a Y-Jaw and an X-Jaw. Computer 40, in conjunction with dose control unit 50, controls the Y- and X-jaws using drives 56 and 58. As will be described in further detail below, X-jaw drive 56 and Y-jaw drive 58 operate independently, allowing beam 52 to be shaped with greater precision and control. X-jaw and Y-jaw drives 56 and 58 are also used to control individual elements which form the X- and Y-jaws and which will be discussed in further detail below. In some embodiments, X-jaw and Y-jaw drives 56 and 58 may also have independent hand controls to allow an operator of the radiation therapy device to adjust a beam shape by hand (e.g., during treatment pre-planning). The positions of the X and Y-jaws are controlled using drives 56 and 58 in conjunction with one or more sensors 57, 59.

In one embodiment, computer 40 may be operated to place the X- and Y-jaws in a prescribed position before treatment. According to embodiments of the invention, the position of both the X and Y-jaws may be manipulated as well as the position of the individual elements forming the X-jaws. The result is a system which allows a great degree of control over the shape of a beam at the treatment zone. For example, where the radiation beam is an X-ray beam, the position of both the X and Y-jaws and the elements forming the X-jaws can be manipulated such that surfaces of the elements and the jaws are relatively perpendicular to a long axis of the tumor being treated. As another example, where the radiation beam is an electron beam, the position of both the X- and Y-jaws can be manipulated with great accuracy to compensate for in air attenuation and scattering of the electron beam. A more precise and therapeutic beam may thus be delivered to the treatment zone.

In other embodiments, either or both of the X- and Y-jaws (and the individual elements of the X-jaws) may be manipulated by computer 40 during treatment to vary a shape of the beam to deliver a prescribed radiation dose to a treatment area. Further, the enhanced control of both the X- and Y-jaws (and the individual elements of the X-jaws) provided by embodiments of the present invention may also be used to deliver more precise treatment where a mixed beam modality (X-ray and electrons) is used. When a mixed beam modality is used, embodiments of the present invention permit precise control over beam shape while taking into account different attenuation, scattering, and other affects for the two types of beams. Individual element positions will be determined based on a given electron energy and based on the effects of attenuation, scattering, and loss of lateral electronic equilibrium.

Figure 3:
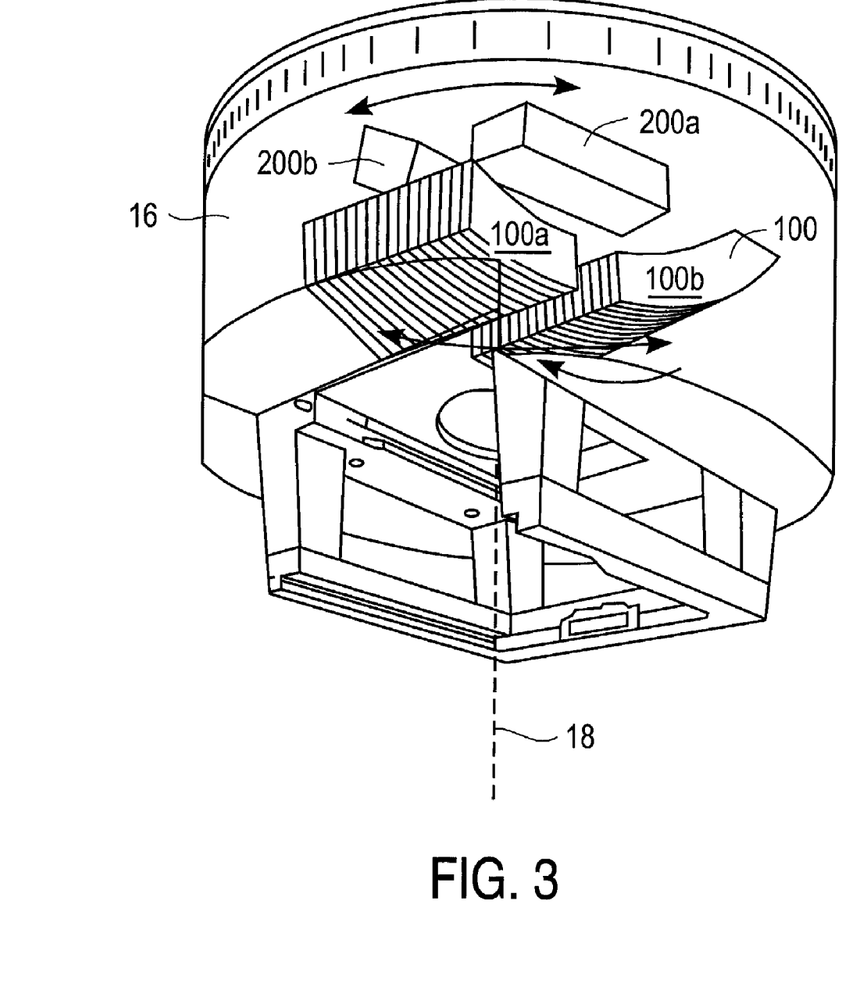
FIG. 3 is a diagram illustrating a treatment head for use in a radiation therapy device according to one embodiment of the present invention.

Referring now to FIG. 3, a cross-sectional view of treatment head 16 is shown. In some radiation therapy devices 10, such as the device shown in FIG. 1, treatment head 16 is coupled to gantry 12, and the entire structure is rotatable about an axis 14 (as shown in FIG. 1). Treatment head 16 is an assembly which contains, among other devices, a collimator structure, shown as X-jaws 100a, 100b, and Y-jaws 200a, 200b. X-jaws 100a, 100b are disposed between Y-jaws 200a, 200b and the patient. X-jaws 100a, 100b are positioned parallel to an X-axis, Y-jaws 200a, 200b are positioned parallel to a Y-axis (where axis 18 is the Z-axis). The positioning of X-jaws and Y-jaws form a generally rectangular opening through which the radiation beam passes along axis 18. Embodiments of the present invention permit greater control of both the X-jaws (and individual elements of the X-jaws) and the Y-jaws, allowing greater control of the shaping of the beam as it passes between the X- and Y-jaws through treatment head 16.

Each of the X- and Y-jaws 100, 200 are formed of radiation attenuating material. In one embodiment, the jaws are formed of material which has x-ray transmission characteristics of less than 1%. For example, tungsten is a currently preferred material, although other materials with similar radiation attenuating characteristics may be used.

According to one embodiment of the present invention, X-jaws 100a, 100b and Y-jaws 200a, 200b are independently controlled (e.g., by motor control 54, X-jaw drive 56, and Y-jaw drive 58 as described in conjunction with FIG. 2, above). The jaws may be controlled in a number of different ways. For example, in one embodiment, X-jaws 100a, 100b and Y-jaws 200a, 200b are independently rotatable about axis 18 (e.g., from −180 degrees to +180 degrees). Further, as depicted in FIG. 3, X-jaws 100a, 100b may be formed of a plurality of individual elements 102a–n, 104a–n. Movement of each of these individual elements 102a–n, 104a–n may be controlled (e.g., by motor control 54 and X-jaw drive 56) along a path intersecting axis 18. Independent movement of each of these items, according to the invention, allows greater control and flexibility in defining a beam shape at the treatment zone 22. This allows more accurate delivery of a proper radiation dose to the treatment zone 22 without damage to surrounding tissue and organs.

Figure 4:
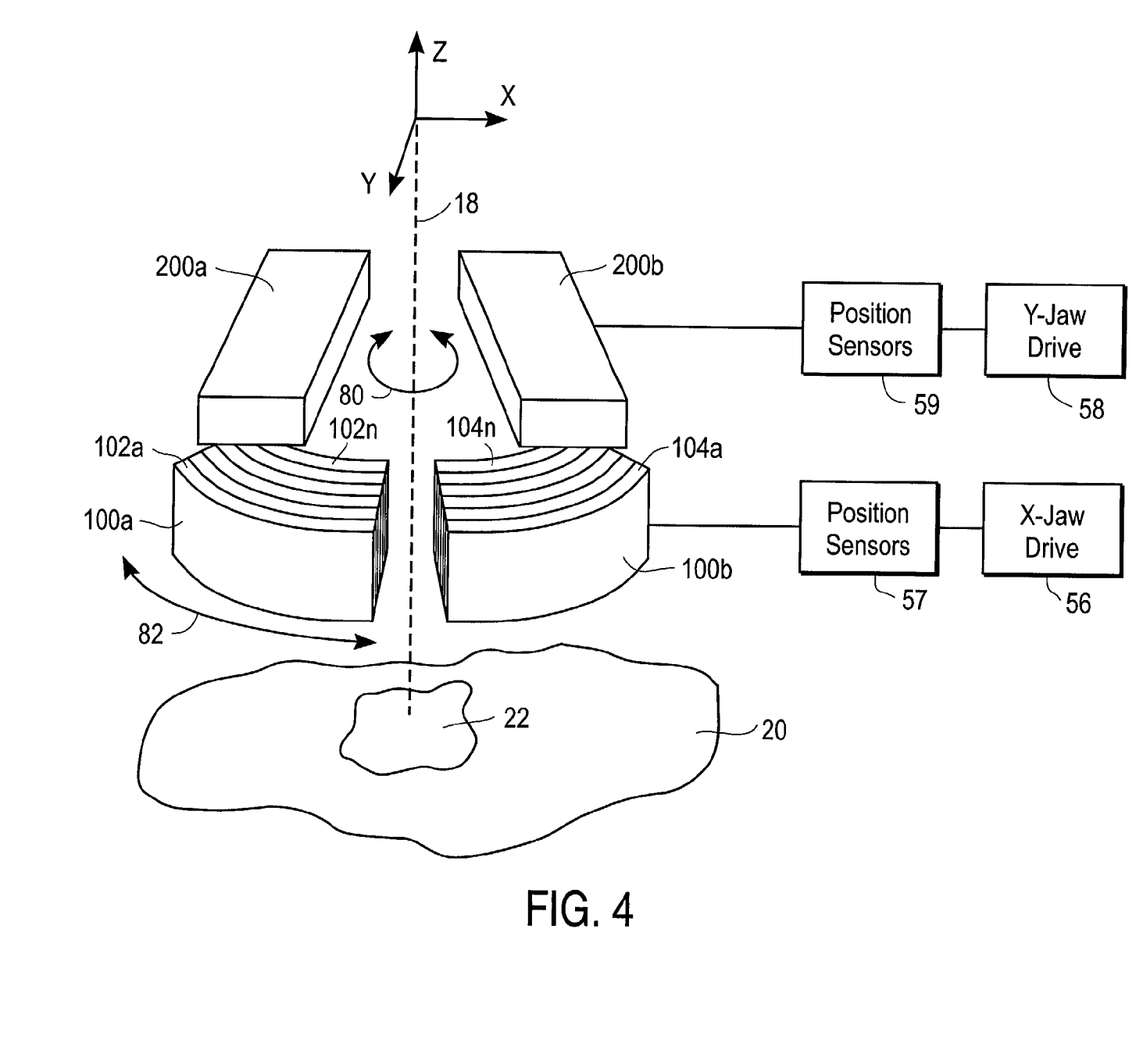
FIG. 4 is a diagram illustrating a collimator for use in a radiation therapy device according to one embodiment of the present invention.

Further details regarding the collimator are shown by referring now to FIG. 4. Y-jaws 200a, 200b are shown positioned above X-jaws 100a, 100b. Axis 18, along which the radiation beam is directed, passes through an opening defined by Y-jaws 200a, 200b and X-jaws 100a, 100b towards treatment zone 22 of body 20. According to embodiments of the present invention, X-jaws 100a, 100b and Y-jaws 200a, 200b are each independently rotatable in a direction 80 about axis 18. Movement and positioning of Y-jaws 200a, 200b are controlled by one or more position sensors 59 coupled to Y-jaw drive 58. Movement and positioning of X-jaws 100a, 100b are controlled by one or more position sensors 57 coupled to X-jaw drive 56.

X-jaws 100a, 100b are each formed of a number of elements 102a–n, 104a–n which are movable in a direction 82 across axis 18. Movement of each element 102, 104 is separately controllable, allowing a wide variety of beam shapes to be created. In one embodiment, movement of each of elements 102a–n, 104a–n is controlled through use of X-jaw drive 56 in conjunction with one or more position sensors 57. In other embodiments, a separate control mechanism is provided to control movement and positioning of elements 102a–n, 104a–n. In some embodiments, each element will be independently controlled using dual redundant position sensors 57 directly linked to each element.

As depicted, each X-jaw 100a and 100b, and each element thereof, is formed to move in a path having an arc shape selected to maintain the element end matching the beam edge divergence from the source. In one embodiment, movement of each element will be controlled such that the element speed of movement shall be variable from 0.2 mm/sec to 20 mm/sec with minimal ramp-up and ramp-down speeds, although those skilled in the art will recognize that other speeds and control schemes may also be selected to provide a variety of treatment and control options.

According to embodiments of the present invention, a beam shape can be created which more closely matches the shape of treatment zone 22, and in particular, minimizes the number of element or jaw surfaces which are parallel to edges of treatment zone 22. As a result, the effective penumbra and undulation can be reduced, providing a more closely tailored beam shape to treatment zone 22. Applicant has discovered that orientation of each of the elements with respect to the shape of treatment zone 22 is important because the effective penumbra increases substantially as the field edge angle (in degrees) increases. For example, an effective penumbra of 13 mm results from a field edge angle of 80 degrees, while a field edge angle of 0 degrees results in an effective penumbra of 6 mm (as the field edge angle increases, the field edge becomes more parallel to edges of the collimator).

Similarly, applicant has discovered that the undulation of the beam increases substantially as the field edge angle increases. For example, undulation increases from 1 mm to 8 mm as the field edge angle increases from 0 to 80 degrees. To deliver a more conforming treatment beam (with reduced effective penumbra and undulation values), embodiments of the present invention allow both the Y- and X-jaws, as well as individual elements of the X-jaws, to be separately controlled to closely manipulate the portal shape to produce a desired beam shape at treatment zone 22.

Figure 5:
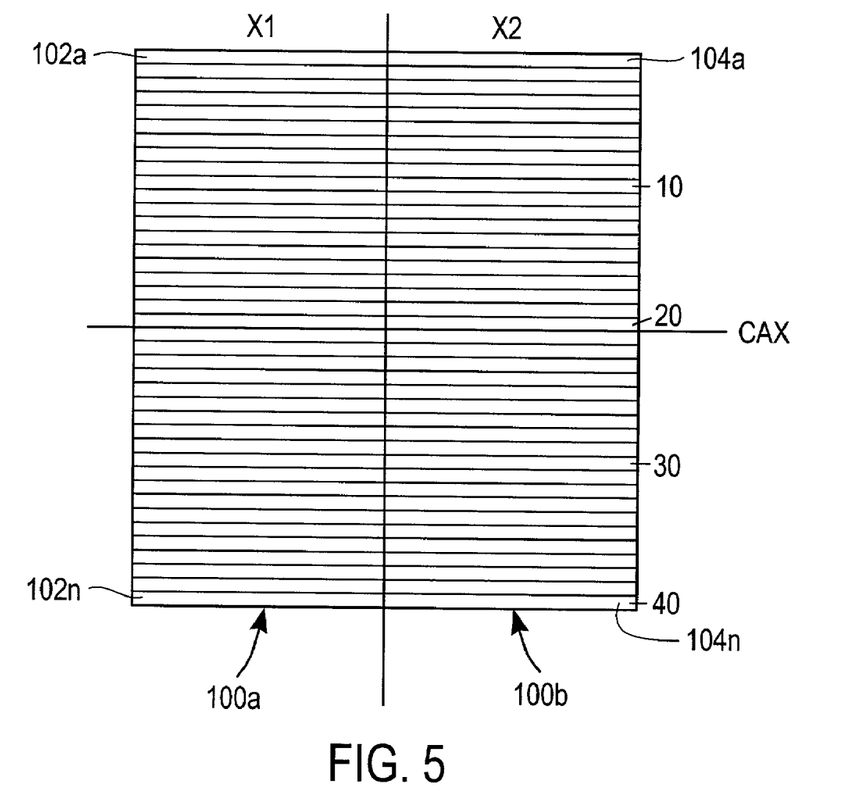
FIG. 5 is a diagram illustrating X-jaws of the collimator of FIG. 4.

Further details regarding the X-jaw will now be described by referring to FIG. 5, where a beam's eye view of X-jaws 100a, 100b is shown. Each of the two blocks forming X-jaw 100a, 100b are formed of a number of individual elements 102a–n, 104a–n. In one embodiment, forty elements are provided in each block 100a, 100b for a total of eighty elements, with the central axis lying between elements number twenty and twenty-one. Each element, in one embodiment, has a 1 cm width resolution, and is independently controlled as described above. In one embodiment, each element has a full range of travel from −10 cm to +20 cm. Those skilled in the art will recognize that other shapes, numbers, and sizes of elements may also be used.

In one embodiment, when radiation therapy device 10 is initialized, each of the elements returns to a default starting position and internal calibrations will be performed to automatically calibrate and sense the position of each element. For example, in embodiments where position sensors 57, 59 include infra-red sensing devices which sense the relative position of the X and Y-jaws, the relative position of each of the elements may be calibrated using infra-red sensing. For example, infrared-sensors may be used to measure a starting position of each of the elements 102a–n and 104a–n allowing precise control of the position of each element during treatment. Those skilled in the art will recognize that a number of other techniques and approaches for calibrating position of elements and jaws may be used.

Figure 6A:
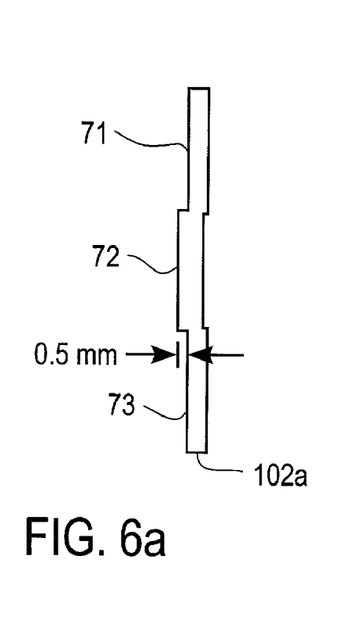
FIG. 6A is a diagram illustrating an end view of an element of the X-jaws of FIG. 5.
Figure 6B:
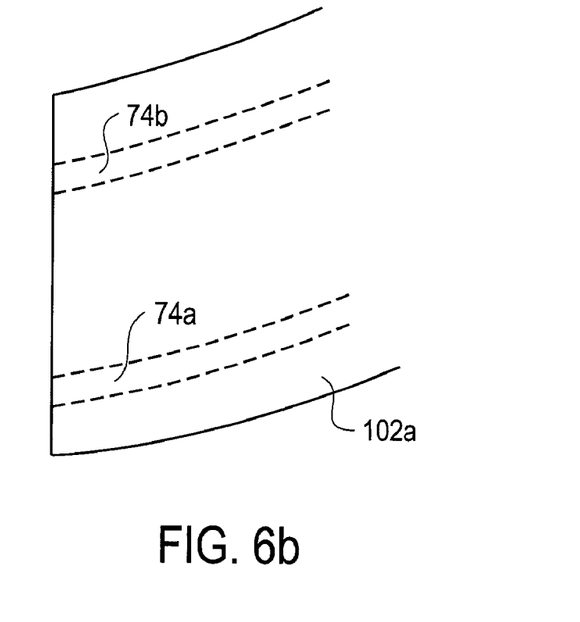
FIG. 6B is a diagram illustrating a side view of the element of FIG. 6A.

Referring now to FIGS. 6A and 6B, details regarding the construction of individual elements will now be described. FIG. 6A depicts an end-view of a single element 102a, showing that each element in one embodiment includes three segments (a top segment 71, a bottom segment 73, and a tongue and groove segment 72), where segments 71 and 73 are equal in length. Tongue and groove segment 72 is utilized to minimize leakage and beam edge penumbra. A side view of element 102a is shown in FIG. 6B showing two bearing tracks 74a, 74b. In one embodiment, alternating bearings are used between individual elements to facilitate movement of each element. FIG. 6B also shows the arc-shape of each element. As described above, each element (and thus X-jaws 100a, 100b) are shaped to move in an arc that maintains the element end to match the beam edge divergence from the source. The result is a system and method which provides a more conforming treatment of treatment zones.

Those skilled in the art will appreciate that various adaptations and modifications of the just-described preferred embodiments can be configured without departing from the scope and spirit of the invention. For example, embodiments of the present invention may be used to support use with beams having a mixed beam modality (e.g., X-rays and electrons). In some embodiments, both the X- and Y-jaws, as well as each of the individual elements of the X-jaws, may be manipulated during a treatment to provide a dynamic approach to field edge smoothing (otherwise known to those skilled in the art as use of a "virtual wedge" producing a wedge dose distribution across the treatment field).

Therefore, it is to be understood that, within the scope of the appended claims, the invention may be practiced other than as specifically described herein.

What is claimed is:

1. A collimator for use in shaping a beam directed along a central axis, comprising:
    a first assembly, rotatable about said central axis, and having a first and a second jaw movable toward each other and toward said central axis; and
    a second assembly, positioned between said first assembly and a treatment zone, said second assembly being rotatable about said central axis independently from the rotation of the first assembly about said central axis, and having a third and a fourth jaw movable toward each other and toward said central axis, said third and fourth jaw each having a plurality of independently controllable elements disposed thereon that are individually operable to move toward said central axis,
    wherein each of said first and said second assemblies and said plurality of independently controllable elements are controllably positionable independently of each other to shape said beam.

2. The device of claim 1, wherein each of said jaws is formed of a radiation attenuating material.

3. The device of claim 1, wherein each of said jaws is formed of a material which has x-ray transmission characteristics of less than or equal to an average of one (1) percent.

4. The device of claim 1, wherein said first assembly is rotatable about said central axis from −180 degrees to +180 degrees.

5. The device of claim 1, wherein said second assembly is rotatable about said central axis from −180 degrees to +180 degrees.

6. The device of claim 1, wherein each of said plurality of elements includes a tongue and groove section for mating with another of said plurality of elements.

7. The device of claim 1, wherein said beam is an X-ray beam.

8. The device of claim 1, wherein said beam is an electron beam.

9. The device of claim 1, wherein said beam has a mixed modality of both X-rays and electrons.

10. A radiation therapy system, comprising:
    a beam generation device, directing a beam along an axis;
    a treatment head coupled to a control device, said treatment head having a first and a second radiation blocking device, said first and second radiation blocking devices independently rotatable by said control device about said axis to selectively shape said beam, said second radiation blocking device further comprising:
        a first jaw and a second jaw, each jaw comprising a plurality of elements disposed thereon that are individually positionable by said control device to move toward each other and toward said axis;
    wherein each of said first jaw, said second jaw, and said plurality of elements are independently positionable by said control device.

11. The radiation therapy system of claim 10, wherein said second radiation blocking device is positioned between said beam generation device and a treatment table.

12. A radiation therapy system, comprising:
    a control device, storing radiation treatment data defining a desired treatment plan;
    a beam generation device, controllable by said control device to deliver a beam along an axis towards a treatment zone;
    a first radiation blocking device, controllable by said control device to rotate about said axis; and
    a second radiation blocking device, positioned between said first radiation blocking device and said treatment zone, controllable by said control device to rotate about said axis independently of said first radiation blocking device, said second radiation blocking device comprising a first jaw and a second jaw, each jaw comprising a plurality of independently controllable elements disposed thereon that are individually operable to move toward each other and toward said central axis;
    wherein said first and said second radiation blocking devices are rotatable about said axis and at least one of said elements are independently controllable to shape said beam according to said radiation treatment data.

13. A radiation therapy method, comprising:
    establishing a treatment plan;
    rotating a first and a second radiation blocking device about an axis to produce a portal shape, said second radiation blocking device comprising a pair of jaws independently rotatable of said first radiation blocking device and having a plurality of elements disposed thereon that are individually movable toward each other and toward said axis;
    adjusting a position of at least one of said plurality of elements to adjust said portal shape according to said treatment plan; and
    directing a radiation beam along said axis toward a treatment zone, said radiation beam shaped by said first and second radiation blocking devices and said plurality of elements of said second radiation blocking device.

14. The radiation therapy method of claim 13, wherein said first and second radiation blocking devices are oriented to conform said portal shape to a shape of said treatment zone.

15. The radiation therapy method of claim 13, wherein said first and second radiation blocking devices are oriented to minimize the effective penumbra of said radiation beam created as said beam passes said first and second radiation blocking devices.

16. The radiation therapy method of claim 13, wherein said first and second radiation blocking devices are oriented to minimize the undulation of said radiation beam created as said beam passes said first and second radiation blocking devices.

17. The radiation therapy method of claim 13, further comprising:
   further adjusting at least one of said first and second radiation blocking devices after directing said beam.

18. The collimator of claim 1, at least one of said plurality of elements having a top segment, a bottom segment and a tongue-and-groove segment disposed therebetween, to minimize beam leakage and beam edge penumbra of the beam.

19. The radiation therapy system of claim 10, at least one of said plurality of elements having a top segment, a bottom segment and a tongue-and-groove segment disposed therebetween, to minimize beam leakage and beam edge penumbra of the beam.

20. The radiation therapy system of claim 12, at least one of said plurality of elements having a top segment, a bottom segment and a tongue-and-groove segment disposed therebetween, to minimize beam leakage and beam edge penumbra of the beam.

21. The radiation therapy method of claim 13, at least one of said plurality of elements having a top segment, a bottom segment and a tongue-and-groove segment disposed therebetween, to minimize beam leakage and beam edge penumbra of the beam.

22. The collimator of claim 1, wherein said elements are formed to move in an arc toward said central axis, a shape of said arc selected to maintain an end of each of said elements to match a beam edge divergence from a radiation source.

23. The radiation therapy system of claim 10, wherein said elements are formed to move in an arc toward said central axis, a shape of said arc selected to maintain an end of each of said elements to match a beam edge divergence from a radiation source.

24. The radiation therapy system of claim 12, wherein said elements are formed to move in an arc toward said central axis, a shape of said arc selected to maintain an end of each of said elements to match a beam edge divergence from said beam generation device.

25. The method of claim 13, wherein said elements are formed to move in an arc toward said central axis, a shape of said arc selected to maintain an end of each of said elements to match a beam edge divergence from a source of said radiation beam.

\* \* \* \* \*